United States Patent [19]

Bartal

[11] Patent Number: 4,734,373
[45] Date of Patent: Mar. 29, 1988

[54] APPARATUS FOR ENHANCING CELL GROWTH, PRESERVATION AND TRANSPORT

[76] Inventor: Arie H. Bartal, Habikurim Street 40, Haifa, Israel

[21] Appl. No.: 877,858

[22] Filed: Jun. 24, 1986

[51] Int. Cl.⁴ ............................................. C12M 1/24
[52] U.S. Cl. ................... 435/296; 435/300; 435/301; 435/284; 215/6; 215/DIG. 3
[58] Field of Search ............... 435/284, 285, 289, 294, 435/296, 298, 300, 301; 215/6, DIG. 3; 220/20, 21

[56] References Cited

U.S. PATENT DOCUMENTS

| | | |
|---|---|---|
| 2,361,992 | 11/1944 | Cantor . |
| 3,065,150 | 11/1962 | Kravitz . |
| 3,532,605 | 10/1970 | Riera . |
| 3,632,478 | 1/1972 | Fink ................... 435/294 X |
| 3,649,464 | 3/1972 | Freeman . |
| 3,655,515 | 4/1972 | Noorlander ............... 435/294 X |
| 3,729,382 | 4/1973 | Shaffer et al. . |
| 3,740,321 | 6/1973 | Pagano et al. . |
| 3,862,886 | 1/1975 | Liner . |
| 3,870,602 | 3/1975 | Froman et al. . |
| 3,886,047 | 5/1975 | Billups, Jr. . |
| 3,898,045 | 8/1975 | Bowley . |
| 3,941,661 | 3/1976 | Noteboom . |
| 3,943,659 | 3/1976 | Katz . |
| 4,030,980 | 6/1977 | Beckford et al. ................ 435/296 |
| 4,053,362 | 10/1977 | Sforza . |
| 4,087,327 | 5/1978 | Feder et al. . |
| 4,104,127 | 8/1978 | Bucalo ............................ 435/296 |
| 4,157,280 | 6/1979 | Halbert ....................... 435/296 X |
| 4,201,845 | 5/1980 | Feder et al. . |
| 4,220,725 | 9/1980 | Knazek et al. . |
| 4,294,924 | 10/1981 | Pepicelli et al. . |
| 4,296,205 | 10/1981 | Verma . |
| 4,326,028 | 4/1982 | Brown ....................... 435/298 X |
| 4,334,028 | 6/1982 | Carver . |
| 4,349,632 | 9/1982 | Lyman et al. . |
| 4,413,058 | 11/1983 | Arcuri et al. . |
| 4,495,289 | 1/1985 | Lyman et al. . |
| 4,514,499 | 4/1985 | Noll . |

*Primary Examiner*—Larry Jones
*Attorney, Agent, or Firm*—Finnegan, Henderson, Farabow, Garrett & Dunner

[57] ABSTRACT

A disposable cell culture device is disclosed. The instant invention finds particular utility in in vitro growth of micro-organisms, plant and animal cells, including germ cells, short and long-term tissue cultures, hybridomas and other biologically engineered cells to maximize the in vitro yield of cell constituents and products. The device comprises an enclosed container having an opening for introducing and removing cells, a plurality of surfaces for supporting cells, each surface having a passage in spaced relationship to each other and mounted in and spaced from the interior walls of the container, and at least one removable cover. The surfaces may be arranged in either a lattice, trapezoidal, conical, pyramidal, honeycomb or other configurations.

11 Claims, 10 Drawing Figures

U.S. Patent  Mar. 29, 1988  Sheet 3 of 5  4,734,373
FIG. 4.
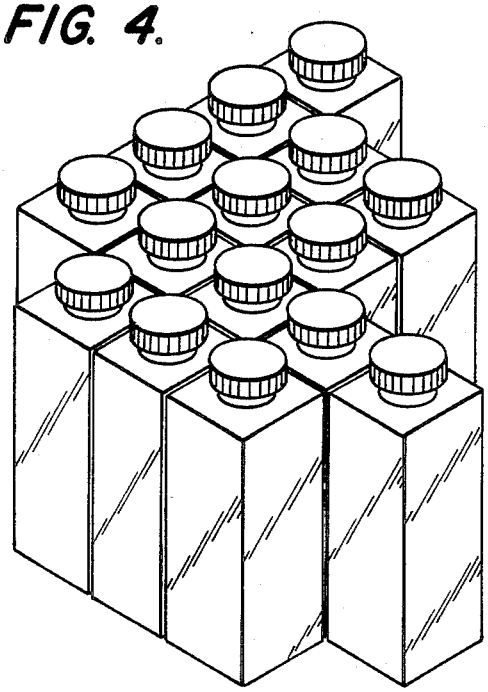
FIG. 5A.
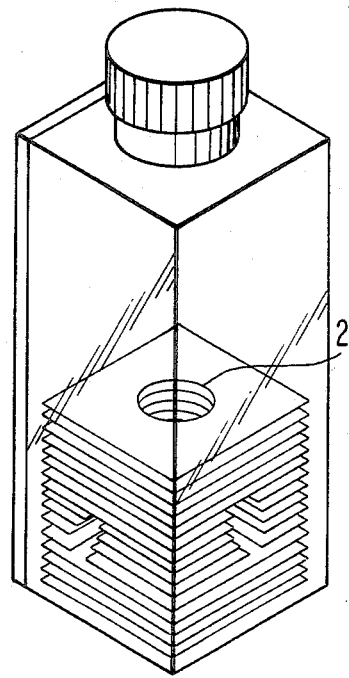
FIG. 5B.
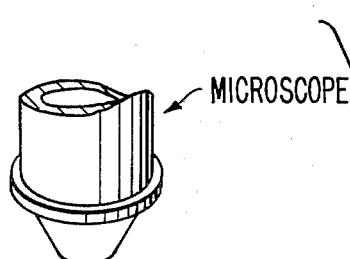
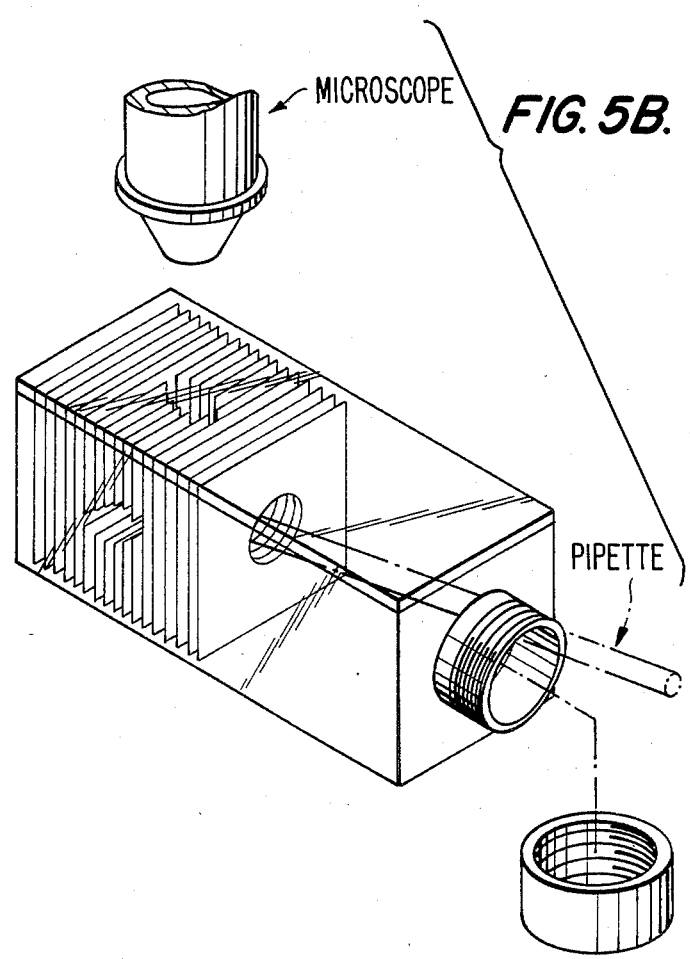

APPARATUS FOR ENHANCING CELL GROWTH, PRESERVATION AND TRANSPORT

BACKGROUND OF THE INVENTION

The present invention relates to newly designed plastic and disposable cell culture devices for widespread use in especially small-scale research laboratories and more particularly relates to functionally-oriented disposable devices integrated with micro-constructed plastic injected cell-culture embodiments generated by a variety of newly-designed micro-architectural engineering. The present invention finds particular utility in facilitating widespread, massive in vitro growth of micro-organisms, plant and animal cells, including germ cells, short and long-term tissue cultures, hybridomas and other biologically engineered cells, to maximize the in vitro yield of cell constituents and products such as monoclonal antibodies or other biologic agents, improve the exposure of cells to various agents, facilitate the investigation of cell to cell interaction improving cell transportation, long-term cell preservation, cell freezing and thawing.

Cell culture refers to the process by which living cells from a variety of sources, animal or plant, are grown and maintained alive in laboratory devices, using artificial culture media to support their basic biological functions. This procedure has become one of the cornerstones in modern animal and plant biology, basic and applied medical research, medical diagnosis and therapy, microbiology, genetic engineering and biotechnology.

Cell culture is also the keystone of in vitro cell fusion technologies, whereby parental cells are fused, either by a chemical or electrical process, or through other fusing processes, to yield newly-formed cells with integrated cytoplasms and nuclei with new biological capabilities, secretory or others, for a variety of purposes. The hybridoma technology is an excellent example whereby parental myeloma cells are fused with parental lymphocytes, to yield immortalized cells called hybridomas, capable of secreting monoclonal antibodies or other cellular factors in endless amounts and high purity. Cell culture is fundamental in other biological fields such as in cellular transfection and genetic engineering, as genes from cells, viruses or other sources are obtained by gene-splitting technologies and then transferred into new hosts to induce massive production of the encoded molecules.

The current art technologies involved for the in vitro growth of cells allow short and long-term maintenance of cells in tissue culture medium, expose cells to a variety of agents, study cell to cell interaction long-term cell preservation by freezing, to yield upon thawing high percentages of viable and functioning cells. Cell cloning is another common cell culture procedure by which heterogenous cell populations are separated by appropriate dilutions into homogenous clones each originating from one parental cell through multiple divisions. Screening efforts of the numerous homogenous clones enables the identification of minute amounts of cell constituents and products present within the waste cell-culture medium, specific for certain clones and thereafter their isolation, purification, characterization and utilization.

The spectrum of modern cell culture procedures can be illustrated by the technology of generating hybridoma clones secreting valuable monoclonal antibodies. The following refers to mouse hybridomas as well as human, rat and other species of hybridomas. While the initial steps involve optimal growth of the parental cell lines and their fusion in the presence of selective medium, the next crucial phases are the screening of cell containing newly-fused clones for their capacity to secrete useful antibodies. Once clones have been selected, the next steps are repeated cloning in the presence or absence of feeder layer cells, expanding the chosen clones, and ultimately obtaining a supernate containing high concentrations of the antibody.

Since hybridoma cell-culture waste medium such as obtained by mouse hybridomas contains limited amounts of antibody, researchers choose to inject hybridoma cells into the abdominal cavity of lipid-primed animals, as illustrated by mice, to induce abdominal fluid called ascitis, highly enriched with monoclonal antibody. While accumulating these hybridoma cells in their abdomens, and while being tapped almost daily to obtain the antibody containing ascitic fluid, these animals gradually become extremely heavy and within a week to three weeks or so stop moving in their cages, cannot reach their water bottles or food, and ultimately die in agony. This is repeated a number of times with numerous mice for each hybridoma clone, and the total number of mice depends on the number of different clones available in the specific laboratory. This procedure is widely used in small-scale research laboratories as well as in large-scale industrial laboratories, and it is estimated that more than thousands of mice and other animals per year are thus utilized for this purpose throughout the scientific community.

Because of a number of causes including rejection phenomena, many types of hybridomas such as human, rabbit, rat and so forth, will not grow within mice or other animals and therefore high titer, monoclonal antibody containing, ascitic fluid cannot be formed in vivo. In these instances the researcher is dependent on tissue culture scale-up procedures depending on the present state of the art. The present invention overcomes these problems and disadvantages of the prior art by generating novel microembodiment containing cell culture devices, enabling every researcher in every small laboratory to generate extremely high titers of antibodies or other cell products, circumventing the necessity of employing abdominal cavities of animals.

Furthermore, this in vitro new art has further advantages as ascitic fluid derived monoclonal antibody is contaminated by a huge variety of animal-derived proteins and other molecules, whereas the scale up procedures involving the present invention are free of this disadvantage.

Once a valuable hybridoma clone has been generated, its long term preservation is of great importance scientifically and economically. Early cell batches of the hybridoma clones are frozen at extremely low temperatures (up to −180° C. or more) depending on the equipment available for freezing. Freezing procedures are harmful and can cause injury to a varying proportion of the cells. It is the objective of the biologist to preserve the viability of as many cells as possible whether using agents such as DMSO (Dimethyl sulfoxide), time-controlled gradual drop in temperature and other means. Current art allows cells to be frozen in monoplane devices such as tubes with flat or round bottom surfaces, and the present invention contributes significant advantages compared to the old art.

Occasionally cell transportation is required between laboratories, and attention is given to preserve their adequacy, sterility and stability. Cells can be transported in a frozen state using dry ice or in other freezing facilities. However, adequate low temperatures cannot be kept for long periods of time such as required when transportation is between countries or continents. Another alternative is transporting viable cells placed within small monoplane tubes or flasks treated with culture medium and kept in room temperature. The above cell culture procedures, as illustrated by the processing hybridoma clones, are essential for other types of cells used in modern biology, or biotechnological experimentation. All above cell maintenance processes are carried out in small-scale pilot research laboratories using disposable uniplanar labware. The present invention comprising a family of newly designed cell handling devices again contributes novel advantages for cell transportation, whether between continents in conventional transportation facilities, or, in the future in space vehicles, into outer space.

The growing of hybridoma cells in abdominal cavities of mice to generate ascitic fluid enriched with monoclonal antibodies is an exception and is associated with the agony caused to the animals used as hosts. Large-scale cell culture facilities employed in biotechnological plants are, by their nature, different from those used in the ordinary small-scale pilot research laboratory. The main goal of the former is massive production of cells and their products for industrial purposes and involves complicated and extremely expensive equipment, demands numerous personnel and is useless for the typical small laboratories engaged in early research and characterization. The unique and outstanding feature of the present invention is the small size simplicity and handiness of the proposed new devices.

Furthermore, the present invention is providing new tools to scientists and will facilitate cellular biology research, particularly cell to cell interation, cell migration, chemotaxis and separation with the identification of novel cell subsets, improved cell exposure to biological, chemical and other agents, cell transformations, transfection and mutation formation, cell fusion technology, in vitro fertilization, and a variety of other cellular behavioral phenomena.

The large-scale facilities utilize multiple roller bottles which are expensive, require intensive labor and carry a high risk of contamination. Other large scale facilities are aimed at increasing the surface of the containers used to grow cells such as roller bottles with one or more annular members placed inside the bottle which are described in U.S. Pat. No. 4,327,886, or a flexible strip wound into a compact cell support to fit inside the roller bottle as described in U.S. Pat. No. 3,853,712, or the use of a plurality of tubes clamped together and fixed to a shaft the entire device being rotated about a shaft placed within a roller-bottle-like apparatus as described in U.S. Pat. No. 3,732,149. Other devices for mass production are disclosed in U.S. Pat. No. 3,827,943 which employs individual tubes to increase the surface, or U.S. Pat. No. 4,514,499 which employs a monolithic support within an assembled composite to immobilize cells with flow providing means. Small scale disposable devices for cell cultures are described in U.S. Pat. No. 4,495,289 and U.S. Pat. No. 3,649,464, both describing multi-well plates all having uniplanar bottoms to grow cells.

One way of increasing the surface area in conventional roller bottles or cell culture devices is to utilize microcarrier beads, artificial capillaries (hollow fibers) and bundle tubes. Microcarrier culture system involve the suspension of millions of individual, minute beads made of gelatin or other materials within tissue culture devices and are not related directly to the present invention. It is worthwhile to notice that these beads are movable, interfere with the direct inspection of the flasks both macroscopically and microscopically and render an increased risk of contamination.

SUMMARY OF THE INVENTION

The present invention overcomes the problems and disadvantages of the prior art regarding monoplane tissue culture devices employed in ordinary non-indusrial, small-scale research by providing micro-constructed plastic-injected cell culture embodiments integrated within newly-designed functionally-oriented, disposable static and handy devices joined in a unitary structure, to facilitate the massive growth and scale-up of cells, to generate high concentrations of cell products such an monoclonal antibodies or other cell constitutents in culture supernates thereby decreasing to a minimum the necessity to use laboratory animals such as mice in a procedure causing ascitis formation and ultimately their death, as well as provide improved art for cell expansion, in vitro stimulation, research design of cell to cell interaction, efficient cell transportation, preservation and freezing.

Current disposable cell culture devices used in small-scale research laboratories, such as flasks, tubes, bottles, dishes or multi-well plates all have monoplane bottoms, upon which cells are transferred and maintained and repeatedly fed with culture media. The micro-constructed embodiments integrated in the frame structure of a whole family of devices disclosed in this invention are disposable, plastic injected, handy and simple facilities designed in new and creative modes primarily to maximally increase the surface upon which cells can proliferate within the given cell culture small scale devices lacking rotary facilities or necessity to maintain culture medium flow and thereby allow massive cell-culture growth with minimal cost, manpower and complications. The huge variation in the micro-architecture of the embodiments adjusting microconstructions allows wide flexibility in the surface within the devices and thus in the growing and maintaining of cells in vitro, in obtaining higher concentrations of antibodies and other cell products in vitro, and in preserving of cells during the freezing process and afterwards. Introducing integrated or removable micro-constructed units within the container allows compartmentalization of the interior volume and therefore novel forms of cellular experimentations and application.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of this invention as embodied and broadly described herein, the cell culture devices of this invention comprises an enclosed container having an interior wall, the container having at least one opening for introducing and removing cell cultures from the container's interior; a plurality of surfaces for supporting cells, each having a plurality of passage means in a spaced relationship to each other mounted in and spaced from the interior wall, the surfaces having edges spaced from the interior wall, and at least one removable cover for maintaining a contamination-free growth environment within the container. The surface can be arranged in either a lattice, trapezoidal, conical, pyramidal, honeycomb or other configurations. Each said surface can also have an opening aligned with an opening on an adjacent flat plate for viewing cell growth and to ease introduction and removal of cells from the container's interior. The container preferably is at least partially transparent. The container may be either a dish, flask, bottle, tube, multi-well plate or any combination of them integrated in novel modes for various functions, and with various materials or appliances placed in at least a part of the borderline in between. Each opening in each surface may be smaller than the opening in the preceeding adjacent surface and larger than the opening in the subsequent adjacent surface to provide a platform for viewing cell growth in each level of the flat plates. The container may also be compartmentalized in order to provide separate environments.

These micro-constructed embodiments are preferably made of transparent plastic-materials such as polystyrene or of materials such as glass, metal and others, according to specific tasks and requirements.

The micro-constructed embodiments integrated in a unitary structure within the bodies of the devices are injected by plastic in a defined molding process to yield a large variety of types of micro-compartments based on different microarchitectural designs. While these micro-constructed embodiment units are integrated in at least one wall of the container, they may be detachable from the container to be transferred into another container whenever such need arises.

Broadly the cell culture embodiment of the present invention comprises multi-planar, multi-compartment micro-constructions integrated within one or several surfaces or part of a surface of the cell culture device in part or most of its enclosed volume.

The micro- and mini-architectural plastic-injected alternatives for micro- and mini-constructions are honeycomb structures, labyrinth-like constructions, multi-planar, multi-level surfaces including, but not limited to conical, trapozoidal, pyramidal or hexagonal forms, all kept apart by networks of rods and braces, cones or fibers, and defined by the molding process determined prior to the plastic injection of the device, according to the specific function of the device and its major way of employment in the handling of cultured cells. Custom-made microembodiment units integrated in a given container may be required for specific types of cell experimentation and usage.

These micro- and mini-constructed multi-planar, multi-compartment embodiments have multiple pores and open spaces of variable diameter and at varying distances on the surfaces to facilitate passage of cells, culture medium, nutrients and gases between the various compartments within the cell culture device and diminish poorly circulated areas within the embodiment-device complex. In particular instances, only cells or predefined diameter may be allowed to migrate out of a given, properly designed microconstructed unit.

The surfaces and compartments within the micro-embodiment have open edges and only rods to keep apart the planes to further ease the even distribution of cells within the growth compartments, deliberate passage of culture medium and dissolved gases. When cells divide excessively, they form confluent layers and the progeny cells are pushed into the open spaces and ultimately into the bottom level.

In accordance with the present invention, predetermined restricted areas will be left monoplanar with no spatial construction to enable visual macroscopic inspection of colonies formed as well as microscopic examination of the proliferating cells within the cell culture device. These areas, varying in number, size and form according to the type, purpose and function of the respective device, will serve as cell yards and balconies to ease the monitoring of the growing cells and are essential for the appropriate inspection of the in-vitro growing cells.

The multi-planar honeycomb, labyrinth-like, conical, pyramidal, trapezoidal or other forms of plastic injected micro- and mini-constructions provide not only extremely large surfaces for cell proliferation but also specifically engineered means to facilitate the possibility to flush cells out of these growth planes and levels for cell harvesting with the help of culture medium.

When the multi-planar micro-architecture is employed, between 2 to 1000 or more levels can be injected depending on the size and design of the device, all separated and kept apart by rods, braces and all porous surfaces capable of carrying large numbers of cells, secreting their products into the culture medium environment to be collected by the biologist, whether monoclonal antibodies, enzymes, cell factors or cell constitutents. These micro-constructions may be employed for maximal cell population exposure to given agents.

In accordance with the present invention, there are a multitude of modes one can creatively design these super-cell culture embodiments and devices and only a minority of suggestions are described herewith or depicted in the enclosed figures.

It will be obvious to those skilled in the art to which the invention pertains, that after understanding the invention, various changes and modifications may be made without departing from the spirit and scope of the invention.

The embodiments integrated within the cell culture devices joined in unitary structures can be injected either with one highly-repeated micro-construction design or consist of a complex of types of architecture and micro-constructional design units in the same container, depending on the function of the device.

The devices into which the embodiments are joined are newly designed according to their function, one of which is to maximally increase the surface for growing cells per given device volume available in the most optimal fashion. For example, in a given device, rectangular shapes of wells, multi-well plates or tubes are used to deliver more space and consequently more growth area than can round-shaped devices. This minimizes the non-functional, wasted areas in between wells in the multi-well plates.

The height and width of the device (e.g. flask, tube, bottle, dish, multi-well plate) is variable and is determined by the size and surface of the embodiment integrated, as well as by the specific function of the device.

When the device containing the micro-embodiment is in the form of a flask or tube, the culture medium is administered through one opening and discarded through the same opening. Cell transfer begins by flooding device and the integrated micro-embodiment with a serum-containing or serum free culture medium appropriate for the growing of the cells. The device is positioned so that the micro-embodiment is covered with the culture medium. The fluid medium level is kept lower than the device aperture to minimize chances of spillage and contamination. When two or more different cell populations or organisms are under investigation, each introduced into a separate micro-embodiment spaced apart within the container, not allowing cells to intermingle, yet the effect exerted one upon the other may be monitored.

The cells are then transferred into the device and after gentle shaking will spread uniformally through the floors, compartments and pores whenever the specific design will allow it to occur. Whenever desirable, cell popualtions may be separated, e.g. by allowing rounded and migrating cells to exit the microembodiment, while the anchorable, or cells exceeding the size of predefined pores, will stay inside.

Two, or a large number of micro-embodiment containing devices are kept one near each other and in a predetermined position to allow cells to settle down and proliferate. While anchorable cells adhere to the surfaces, non-adherable cells grow in suspension. It is due to gravity that these non-anchorable cells tend to accumulate nearby or on the bottom surfaces of the micro-embodiments.

As cells divide, the surfaces are completely covered by the newly formed cells to ultimately form confluent layers. Cells will spread through the pores and multiple openings within the embodiments to empty surfaces and compartments and as they multiply they will fill all empty spaces. In the restricted monoplane areas devoid of construction cells can be inspected microscopically for their morphology, growth pattern and type of colony formed. Within a defined number of days, depending on the number of cells transferred, the whole surface of the device and embodiment becomes covered by cells generated from the monoclonal cell population or multi-clonal source originally transferred into the embodiment.

As cells multiply, the culture medium is consumed faster and has to be changed more often. Ultimately, the rapidly expanding population of cells within the device will have to be fed as often as necessary. In the case of hybridomas and other genetically engineered cells, the supernates withdrawn are collected and stored if containing valuable cells products, such as monoclonal antibodies or other respective factors. Maintenance of the cells growing in the cell culture devices containing the micro-embodiment is standard, similar to the maintenance of monoplane tissue culture labware. Thus these newly designed devices containing actively growing cells can be kept in standard $CO_2$ incubators or containing other gases if necessary with no special expenditures required for monitoring the inside environment. No special sensors are needed in contrast to the monolith culture system with flowing culture medium facilities designed for massive industrial cell growth.

Cells growing within micro-embodiments specifically designed to facilitate cell expansion and in vitro stimulation can be harvested by multiple washings of the embodiment with culture media. Since a number of cells continue to adhere to the surface of the embodiment, these will repopulate the device in large masses of cells within a relative short period of time. In certain instances, solitary microembodiments carrying distinctive subsets of growing cells may be detached from containers to be sterily passed to another container for various purposes. Highly populated, frequently fed, micro-embodiment-containing devices such as flasks of appropriate sizes can provide supernates with very high titers of monoclonal antibodies secreted by hybridoma cells compared to current art for generating such supernates in monoplane devices. These new super-cell-culture devices are intended to diminish to a minimum and completely replace the intra-abdominal administration of hybridomas in mice to generate high titers of antibodies within their abdominal cavities ultimately causing all injected mice to die. Ascitic-derived monoclonal antibodies are contaminated by multiple murine proteins, murine blood cells and viruses, while high-titer supernates produced within the super-cell-culture devices contain only products secreted by the in vitro growing cells and are free of other nonrelated murine contaminants derived from the host.

Thus, the use of these advanced nonexpensive, disposable, handy and laboratory time saving cell-culture devices will enable scientists to save lives of many thousands of mice and other animals per year and more throughout the research community, utilimately dying in agony following the accumulation of ascitis and repeated tapping. These series of newly designed and constructed facilities will also assist in the production of high titer antibody supernates in those cases where hybridomas cannot be injected into animals or in virus-immortalized lymphocytes capable of secreting monoclonal antibodies and in other biological circumstances. Ascitis-derived-monoclonal antibodies are currently used in human therapy. The use of micro-embodiment-containing devices will facilitate production of relatively pure antibodies for these purposes and will also ease the production and characterization of new types of monoclonal antibodies with novel specificities. Furthermore, the disclosed micro-embodiments may be used for in vitro sensitization of lymphocytes prior to cell fusion. The present invention is expected to have a major impact on the biotechnological market and products generated.

The most appropriate devices to be injected by plastics with properly designed micro-embodiments are flasks, tissue culture bottles, dishes, tubes, multi-well plates and any combination of these to be used in ordinary-small-scale laboratories involved in the research and development of monoclonal antibodies and other biological fields. The newly-designed-devices can be produced to almost completely contain the high surface embodiment to maximally utilize the volume enclosed, and yield a maximum increase in surface for cell proliferation. Since the surface can be accurately determined and controlled by the size and architecture of the embodiment integrated within the device, a family of devices with varying surfaces can be generated, to be used for a variety of cell-maintenance-related goals.

When micro-embodiments are incorporated into laboratory tubes, novel advantages for efficient cell-culturing can be achieved. Cells transferred into conventional uniplaner, round-bottom tubes tend, due to gravity, to sediment and form a pellet. With a micro-embodiment integrate within the tube and covered with culture medium, cells can settle and spread on the different levels and compartments of the embodiment to produce confluent layers of cells. While cells within pellets get injured due to clumps formed, especially when kept in pellets for long periods of time as when frozen away, cells that are evenly scattered and grown on surfaces of planes prior to the freezing process tend to be better preserved with high viability whether being frozen for long periods of time, or transported in culture medium in between distinct laboratories.

The micro-embodiment-containing tubes disclosed in the present invention will allow cells to comfortably grow within the compartments and prevent excessive clump formation. When this super-tube is subjected to gradual freezing, the cells within naturally occurring confluent layers will freeze at their specific locations within the multi-planar embodiments and not within pellets or clumps of cells formed in the current monoplanar tubes. Following thawing procedures, cells can be washed out from the super-tube to be transferred into another device, while the residual cell population can be allowed to proliferate within the same micro-embodiment containing tube under appropriate standard incubator conditions after removing anti-freeze and spent medium and refed by fresh culture medium.

Since efficient cell freezing is highly controversial, these new cell culture facilities can enhance capabilities and results. To save space and for better storage efficiency, the novel tubes are designed in a rectangular shape rather than rounded shape as currently manufactured.

A family of devices such as tubes, flasks, bottles and other containers with varying sizes and integrated micro-embodiment surfaces can be generated for creative usage in cell maintenance. It is needless to emphasize that all these micro-embodiment containing devices may be coated with various biological molecules whenever indicated such as collagen, connective tissue matrix and others to simulate in vivo conditions. Thus, in addition to usage in cell freezing, these novel devices as illustrated by tubes, can be used for cell transportation between laboratories of different countries and continents and in the future can be employed in cell transportation in the outer space. Initially cells are allowed to grow throughout the surface of the micro-embodiment and then, at an optimal growth phase, the whole device is filled with culture medium, the top is tightly closed and then the tube can be readily transported.

Micro-embodiments integrated into dishes or cell-culture wells of multi-well plates will increase the internal growth surface within these devices. To utilize the multi-well plates in a more optimal fashion, and to minimize non-functional areas, the wells containing the micro-embodiments are designed rectangular instead of round in shape, thus increasing volume of each well and consequently the size and surface of the integrated embodiment. Furthermore, the height of each well is increased to enable the integration of larger micro-embodiments into the wells. Micro-embodiment-containing multi-well plates allow growing larger number of cells within each well and therefore supernates may contain higher titers of monoclonal antibodies when hybridomas are grown, or higher concentrations of other cellular factors when other types of cells are grown. The presence of higher titers of antibodies will ease the identification of novel useful hybridoma clones in selected wells currently negative by conventional art and thus assist in more efficient screening procedures of hybridomas or other clones generated in modern biological and genetic engineering assays.

The super-multiwell plates integrated with micro-embodiments can also be used for freezing of high numbers of viable and well-distributed cells prior, during or after the processes of screening or cloning according to the convenience of the biologist and can also save time. The management of these plates is similar to the conventional uni-planar multi-well plates, concerning pipetting, use of incubators, hoods and other facilities common in the market.

These high surface, newly designed, micro-embodiment containing devices joined in a unitary structure and disposable for common use, render new capacities to growing cells in culture, in their maintenance, and are useful in a wide range of cell-culture procedures in a non-expensive manner. In addition to the advantages described above, this invention is expected to arm the scientist and clinician involved in laboratory research with new facilities that will enable them to design novel experiments in the field of biology including microbiology, biochemistry, human diseases, and related areas. New achievements will be made in the fields of cell to cell interaction, cell and micro-organism interaction, symbiotic and antagonistic phenomena, cell migration, chemotaxis, cytotoxicity, cell fusion, cellular subsets and heterogeneity and many other related fields.

The accompanying drawings which are incorporated in and constitute a part of this specification, illustrate embodiments of the invention and, together with the description, serve to explain the principles of the invention.

BRIEF DESCRIPTION OF THE DRAWINGS

FIG. 4 is a perspective view of flasks or tubes described in FIG. 3.

FIGS. 5A and 5B are perspective view of flasks or tubes containing micro-embodiments.

DESCRIPTION OF THE PREFERRED EMBODIMENTS

Reference will now be made in detail to the presently preferred embodiment of the invention, an example of which is illustrated in the accompanying drawings.

Figure 1:
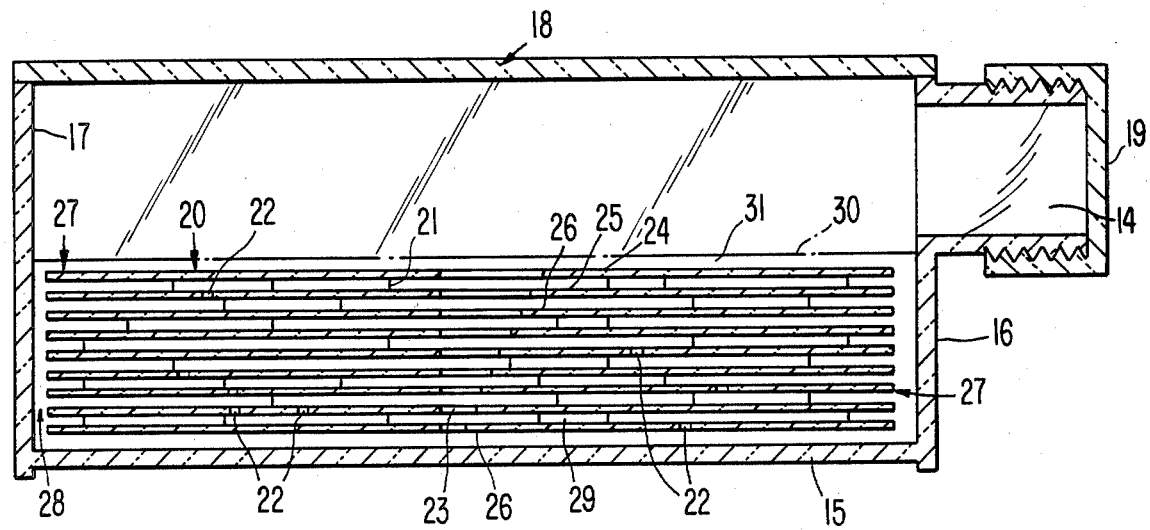
FIG. 1 is a side view of a cell culture micro-embodiment integrated within a tissue culture flask.

The preferred embodiment of the cell culture device is shown in FIG. 1 and includes a base (15), walls (16, 17) and a micro-constructed embodiment (20) integrated in a unitary structure with the base (15). An outlet-inlet opening 14 is shown to be opened or closed by a screw-type top (19). The top (19) may be completely removed from the device and can be mounted on the device.

Figure 2:
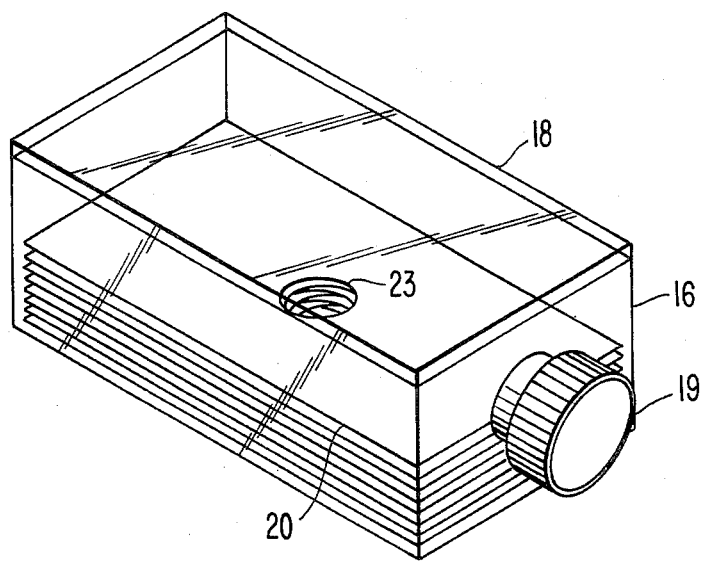
FIG. 2 is a perspective view of a cell culture device with an integrated micro-embodiment in the base of the flask.

The micro-constructed embodiment (20) is designed in the device illustrated in FIGS. 1 and 2, as a multi-planar multi-compartment embodiment having a plurality of layers kept apart by rods (21) with multiple pores 22 present in each one of the surfaces. In the center of the embodiment of space 23 is created with no micro-construction to allow visual microscopic and microscopic examination of the cells growing on the base 15 of the device through the top wall (18). The multi-planar embodiment (20) is designed to allow the surfaces directed toward the center of the embodiment to terminate in different lengths (24, 25, 26) thus generating on each level a balcony, enabling microscopical examination of the growing cells through the top wall (18) on each one of the exposed balconies (24, 25, 26) of the plurality of layers of the embodiment.

The micro-embodiment integrated with the base (15) of the device is kept apart from the side walls (16), thus a space is created between the ends 27 of the layers and the walls (16) that communicates with the extra-embodiment space 31 above the embodiment of that space 23 existing within the embodiment at its center, devoid of construction.

All surfaces of the micro-embodiment end in all directions with no walls, thus opening freely into the internal space(s) (23) or extra-embodiment spaces 31 of the device. Both extra- and intra-embodiment spaces are filled by cell culture medium prior to the allocation of cells into the device. This tissue culture medium is transferred into the device through the opening (14) up to a level 30 kept above the micro-embodiment (20) but still below the opening.

The extra-embodiment space 31 combines with the intra-embodiment spaces through the open edges (27) of the surfaces of the micro-embodiment 20 and pores 22 within the surfaces, to form one large continuous space to facilitate passage of cells, culture medium, nutrients and gases between the different compartments within the device.

The inlet-outlet of the flask shown in FIGS. 1 and 2 on a sidewall (16) can also be located on the upper wall (18) or on any other location according to the planned function of the flask. The micro-embodiment (20) can be designed to occupy different proportions of the volume enclosed within the shown flask according to the functional role of the flask. It thus can be expanded and constructed throughout the whole internal volume of the device in accordance with the guidelines described above to allow complete communication between the various levels and compartments within the embodiments.

Figure 3:
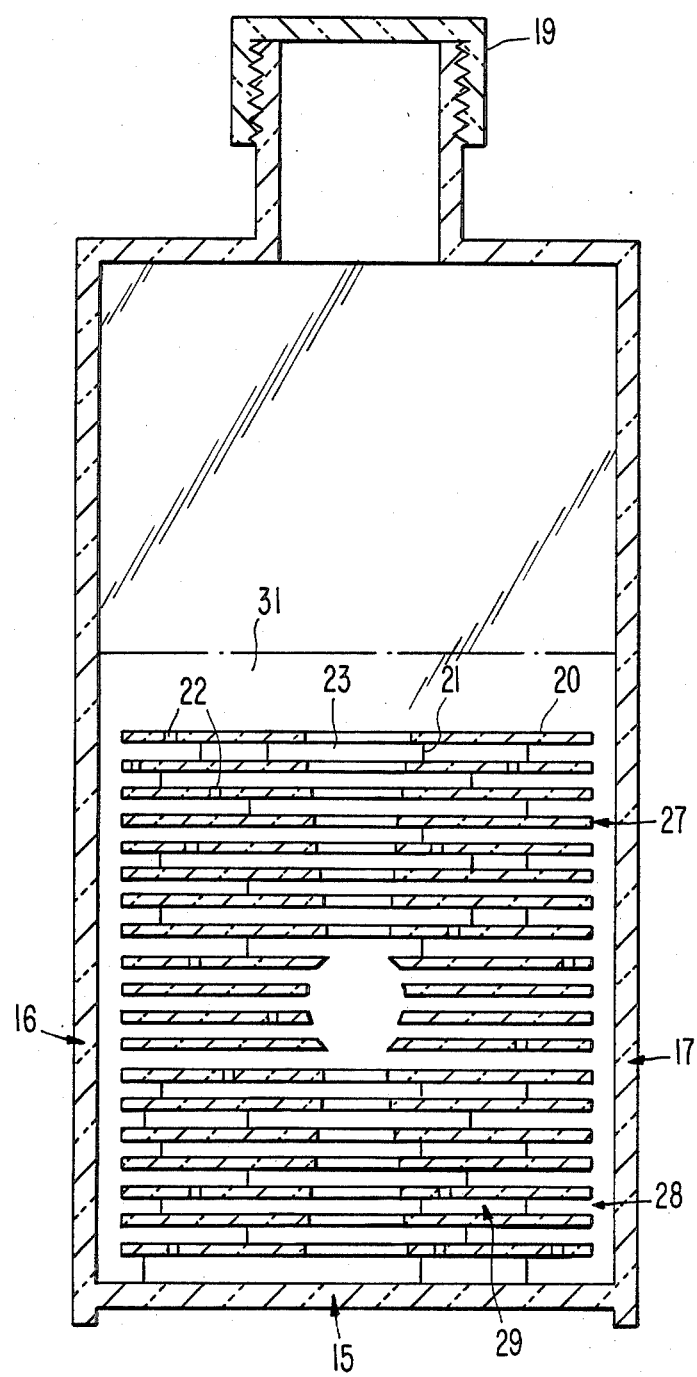
FIG. 3 is a side view of a cell culture device, either flask or tube, integrated with a high surface micro-embodiment.

FIG. 3 illustrates a cross section of a flask or tube, that includes a base (15), walls (16, 17) with an inlet-outlet on the top and a micro-construction (20) included within the device, constructed above the base surface (15). The micro-embodiment is constructed of multi-level surfaces kept apart by multiple rods (21) with no continuous walls allowed to prevent stagnation. The surfaces comprising the embodiments have pores (22) allowing circulation of medium and passage of cells between the various compartments 29. These surfaces are free at their ends to allow the space inbetween the surfaces to communicate with the extra-embodiment (28) space 23 between the embodiment and the walls of the device (16, 17) or the space above the embodiment.

Certain spaces 23 designed within the embodiment are devoid of micro-constructions, to allow visual macroscopic and microscopic examination of colonies or cells, respectively, growing on the bottom level (15).

FIGS. 4, 5A and 5B illustrate flasks or tubes from an oblique angle to depict the micro-embodiment enclosed with the tissue culture device. The multi-planar surfaces are kept apart by rods and braces as shown in FIG. 3, and all surfaces end freely with no barriers to allow maximum freedom for circulation and passage of cells as described above.

One or more central or peripheral areas are allowed with no construction, not only to enable visual examination of colonies growing on the uni-planar surfaces, but also to allow even administration of cells or their harvesting using conventional pasteur pipettes or other types of pipettes. The intra-embodiment spaces communicating with the extra-embodiment spaces facilitate this even distribution whether through each single plane or through the open central spaces (23).

Figure 6:
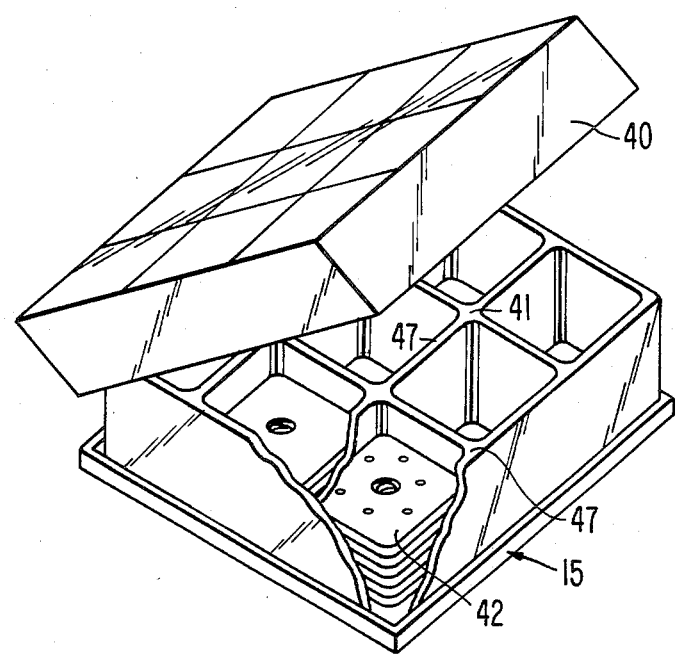
FIG. 6 is a fragmentary cross-sectional view of a multi-well plate with each rectangular well containing an integrated micro-embodiment.
Figure 9:
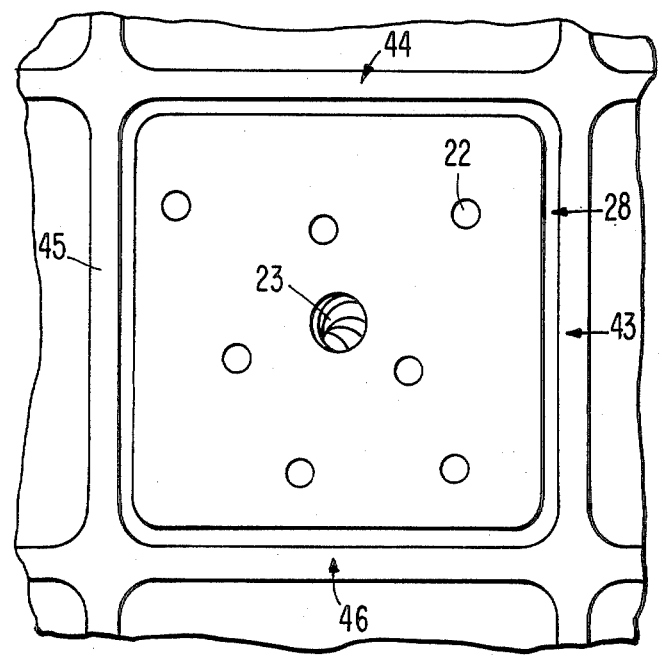
FIG. 9 is an elevation view of a well or dish containing a micro-embodiment showing the structure of one plane within the embodiment as seen from above.

FIG. 6 shows a tissue culture plate that includes a base (15) with rectangular wells (41) and a cover (40). The cover (40) can be completely removed from the base. The base (15), cover (40) and the planes composing the micro-embodiments (42) are all made of transparent plastic materials such as styrene, made by the injection molding process. The base of each rectangular well (15) is injected by plastics according to the mold in one unitary structure with the micro-embodiment complex (42). Each well (FIG. 9) has four sides (43, 44, 45, 46) extending upwards from the bottom base (15) and are in direct contact inwardly with the extra-embodiment space (28).

The micro-embodiment consists of multi-planar, multi-compartment high surface plastic-injected structure. The planes (27) have pores (22) at varying distances and are kept apart by rods (21) to decrease the possibility of internal blockage, and enhance internal passage of nutrients and gases within the micro-embodiment.

All ends (27) of the micro-embodiment planes are left free with no walls or barrier to further enable easy communication between the internal and extra-micro-embodiment spaces 28. Each plane has its pores (22) and passages to planes above and below. In the center of each plane there is a large space (23) to communicate with a similar space in the planes above and below, to form a wide channel for introducing pipettes (23). This compartment with no micro-construction enables direct visual inspection of the bottom base (15) of the wells for the monitoring and evaluation of the growing cells.

The bottom wall (15) typically may be 0.05 inch in thickness and the mold from which the base is made is carefully machined so as to provide a very high degree of transparency for the bottom wall, as well as for the other walls of the cell culture device.

Figure 7:
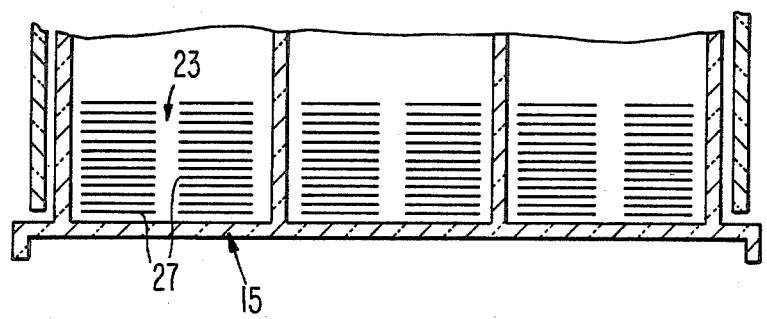
FIG. 7 is a side view and cross section of a multi-well plate showing the integrated micro-embodiment within each well.
Figure 8:
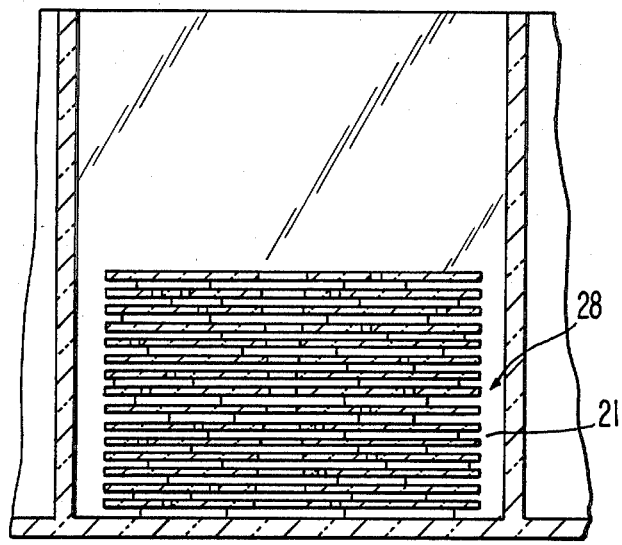
FIG. 8 is a side view of one well within a multi-well plate showing the integrated micro-embodiments within each well.

In the multi-well plate shown in FIGS. 6 and 7, the base (15) is designed with separate rectangular wells (41), their number ranging between 2 to at least 120, all capable of receiving the tissue culture or other materials to be cultivated or otherwise investigated in the dish. Each well is formed by 4 walls (43, 44, 45, 46) that extend upwardly from the upper surface of the bottom wall (15) to their upper edges 41 which are co-planar and lie in a plane parallel to the bottom wall (15).

The wells measured from the upper surface of the bottom well which defines the bottom of the wells to the edges (41) may be 0.70 inch, however its height is flexible and determined according to the role of the plate to be used in a variety of tissue culture procedures. The number of wells and their arrangement will be determined for each device according to the intended use, e.g. screening, freezing or expending of cells. A series of super-plates are generated depending on the surface of the base and height of the wells, each type to yield known increase in the surface of the well.

An important aspect to be emphasized is the unused surface (47) in between the rectangular wells which is to be minimized and thus the actual growth surface in the whole plate will increase. The total area of all wells present in the multi-well plate, used for growing cells will be as close as possible to the total area of the base (15) of the whole plate, to provide maximum efficiency.

It will be apparent to those skilled in the art that various modifications and variations can be made in the cell culture device of the present invention without departing from the scope or spirit of the invention. Thus, it is intended that the present invention cover the modifications and variations of this invention provided they come within the scope of the appended claims and their equivalents.

What is claimed is:

1. A cell culture device comprising:
   an enclosed container having interior walls and at least one opening for introducing and removing cell cultures from said container's interior;
   at least one multi-planar structure mounted within the container and having a plurality of surfaces for growing cells, each surface having a plurality of pores and being mounted in spaced relationship to each other with their edges spaced from said interior walls to permit communication between the surfaces;
   each said surface having an opening aligned with an opening in an adjacent surface with the opening on a surface interior of an adjacent surface being smaller than the opening in said adjacent surface to permit viewing and introduction and removal of cells from each surface of the multi-planar structure.

2. A cell culture device as defined in claim 1 wherein said surfaces are arranged in a conical configuration.

3. A cell culture device as defined in claim 1 wherein said surfaces are arranged in a pyramidal configuration.

4. A cell culture device as defined in claim 1 wherein said surfaces are arranged in a trapezoidal configuration.

5. The cell culture device of claim 1 including a plurality of spaced supports positioned between said surfaces to maintain the spaced relationship between said surfaces.

6. The cell culture device of claim 1 wherein at least a portion of said container is transparent to permit viewing of the cells from the exterior of the container.

7. The cell culture device of claim 1 wherein said container is a bottle.

8. The cell culture device of claim 1, wherein the surfaces of the multi-planar structure are parallel to one another.

9. The cell culture device of claim 1 wherein said container is a multi-well plate.

10. The cell culture device of claim 9, wherein each well contains a separate multi-planar structure to provide a plurality of separate environments for the growing of cells.

11. The cell culture device of claim 1 wherein said multi-planar structure is removable from the container.

* * * * *